(12) United States Patent
Chung et al.

(10) Patent No.: US 10,594,400 B2
(45) Date of Patent: Mar. 17, 2020

(54) FREE SPACE OPTICAL COMMUNICATION-ENABLED TEXTILE ASSEMBLY

(71) Applicant: Advanced Functional Fabrics of America, Inc., Cambridge, MA (US)

(72) Inventors: Chia-Chun Chung, Malden, MA (US); Jason Cox, Ashland, MA (US); Yoel Fink, Brookline, MA (US); Mihai Ibanescu, Somerville, MA (US); Chhea Chhav, Dracut, MA (US)

(73) Assignee: Advanced Functional Fabrics of America, Inc., Cambridge, MA (US)

( * ) Notice: Subject to any disclaimer, the term of this patent is extended or adjusted under 35 U.S.C. 154(b) by 0 days.

(21) Appl. No.: 16/006,343

(22) Filed: Jun. 12, 2018

(65) Prior Publication Data
US 2019/0007139 A1 Jan. 3, 2019

Related U.S. Application Data
(60) Provisional application No. 62/520,944, filed on Jun. 16, 2017.

(51) Int. Cl.
*H04B 10/2581* (2013.01)
*H04B 10/112* (2013.01)
(Continued)

(52) U.S. Cl.
CPC ......... *H04B 10/2581* (2013.01); *H04B 10/11* (2013.01); *H04B 10/112* (2013.01);
(Continued)

(58) Field of Classification Search
CPC .. H04B 10/2581; H04B 10/11; H04B 10/803; H04B 10/2587; H04B 10/112;
(Continued)

(56) References Cited

U.S. PATENT DOCUMENTS

| | | |
|---|---|---|
| 4,234,907 A | 11/1980 | Daniel |
| 6,381,482 B1 | 4/2002 | Jayaraman et al. |

(Continued)

FOREIGN PATENT DOCUMENTS

WO  WO-2018/022856 A1   2/2018

OTHER PUBLICATIONS

International Search Report and Written Opinion for International Patent Application No. PCT/US2018/037080, dated Sep. 24, 2018 (11 pages).

(Continued)

*Primary Examiner* — John Bedtelyon
(74) *Attorney, Agent, or Firm* — Goodwin Procter LLP

(57) ABSTRACT

A textile capable of detecting electromagnetic radiation includes interlaced fibers; a photodetector embedded, as a result of a fiber draw process, within a particular one of the fibers; and a first electrical conductor extending within the particular fiber and along a longitudinal axis thereof. The first electrical conductor is in electrical contact with the photodetector, and the photodetector position in the particular fiber corresponds to a lowest energy configuration relative to a pattern of flow along the longitudinal axis of the particular fiber throughout the fiber draw process. A method of manufacturing the textile and a system including the textile are also disclosed.

21 Claims, 7 Drawing Sheets

(51) Int. Cl.
| | |
|---|---|
| *H04B 10/11* | (2013.01) |
| *H04B 10/2587* | (2013.01) |
| *H04B 10/80* | (2013.01) |
| *A61B 5/00* | (2006.01) |
| *B29D 11/00* | (2006.01) |

(52) U.S. Cl.
CPC ....... *H04B 10/2587* (2013.01); *H04B 10/803* (2013.01); *A61B 5/0017* (2013.01); *A61B 5/6802* (2013.01); *B29D 11/00721* (2013.01)

(58) Field of Classification Search
CPC ............ B29D 11/00721; A61B 5/6802; A61B 5/0017; A61B 5/6803; A61B 5/6804; A61B 5/6805; A61B 5/6806; A61B 5/6807; A61B 5/6808
See application file for complete search history.

(56) References Cited

U.S. PATENT DOCUMENTS

| | | | |
|---|---|---|---|
| 7,953,326 | B2 | 5/2011 | Farr et al. |
| 8,417,120 | B2 | 4/2013 | Kim et al. |
| 2017/0354372 | A1* | 12/2017 | Varadan ............. A61B 5/04085 |
| 2018/0039036 | A1 | 2/2018 | Fink et al. |

OTHER PUBLICATIONS

Chan et al., "MouseVLC: Visible Light Communications using Mouse Sensors", IEEE International Conference on Internet of Things (iThings 2014), IEEE Green Computing and Communications (GreenCom), and IEEE Cyber, Physical, and Social Computing (CPSCom), 2014. (Abstract Only).

Chen et al., "A Framework for Simultaneous Message Broadcasting Using CDMA-Based Visible Light Communications", IEEE Sensors Journal, vol. 15, No. 12, Dec. 2015. (Abstract Only).

Chi et al., "450-nm GaN laser diode enables high-speed visible light communication with 9-Gbps QAMOFDM", Optics Express, vol. 23, No. 10, pp. 13051-13059, May 8, 2015.

Chun et al., "Demonstration of a Bi-directional Visible Light Communication with an overall Sum-rate of 110 Mb/s using LEDs as Emitter and Detector", IEEE Photon. Conf., pp. 132-133, Oct. 2014.

Classen et al., "The Spy Next Door: Eavesdropping on High Throughput Visible Light Communications", Proceedings of the 2nd International Workshop on Visible Light Communications Systems, pp. 9-14, ACM, 2015.

Elgala et al. "Indoor Optical Wireless Communication: Potential and State-of-theArt", IEEE Communications Magazine, pp. 56-62. Sep. 2011.

Fink, "Realizing a Moore's Law for Fibers", SPIE Defense + Commercial Sensing, Abstract, Apr. 9, 2017, p. 141.

Liu et al., "Visible Light Communication Using Receivers of Camera Image Sensor and Solar Cell", IEEE Photonics Journal, vol. 8, No. 1, pp. 8, Feb. 2016.

Santos et al., "Visible Light Communication using InGaN optical sources with AlInGaP nanomembrane down-converters", Optical Society of America, vol. 24, No. 9, pp. 10020-10029, Apr. 28, 2016.

Tian et al., "Poster: Visible Light Communication in the Dark", Mobicom '15, pp. 3, Sep. 2015.

Uysal et al., "Optical Wireless Communications—An Emerging Technology", 16th International Conference on Transparent Optical Networks (ICTON), 2014. (Abstract Only).

Wang et al., "Distributed Load Balancing for Internet of Things by using Li-Fi and RF Hybrid Network", IEEE 26th Annual International Symposium on Personal, Indoor, and Mobile Radio Communications (PIMRC): Mobile and Wireless Networks, 2015. (Abstract Only).

* cited by examiner

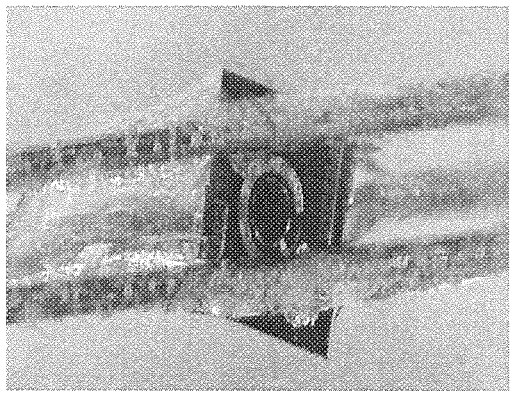
Figure 8A
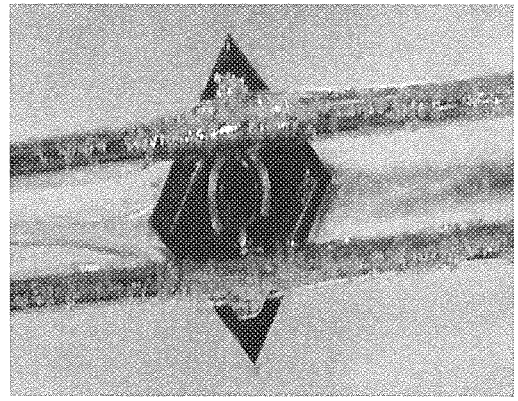
Figure 8B
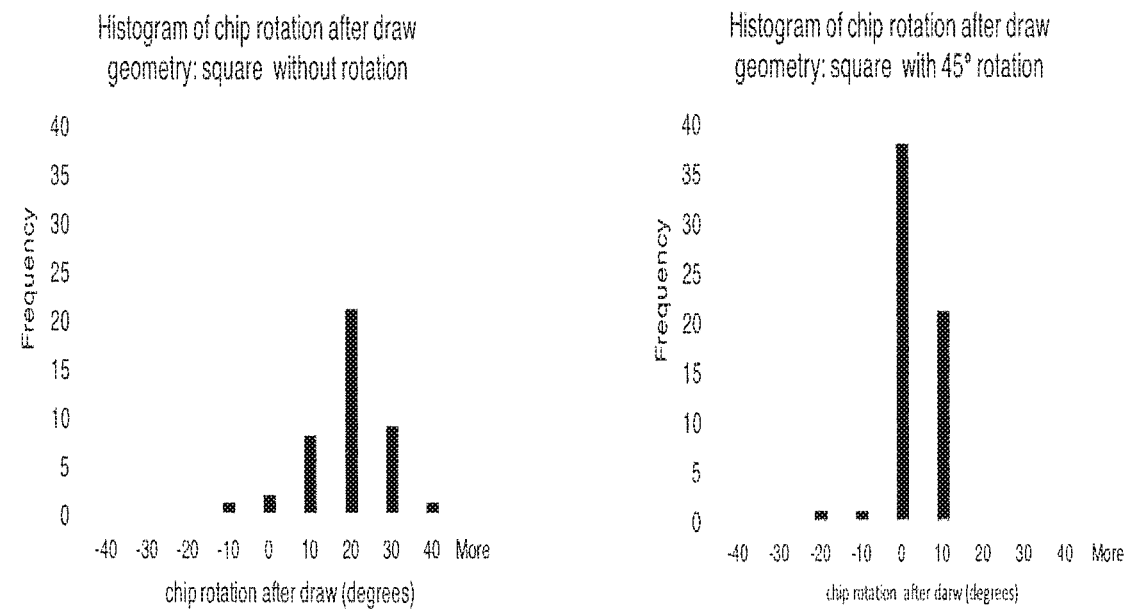
Figure 9A
Figure 9B

FREE SPACE OPTICAL COMMUNICATION-ENABLED TEXTILE ASSEMBLY

CROSS-REFERENCE TO RELATED APPLICATION

This application claims priority to and the benefit of, and incorporates by reference herein in its entirety, U.S. Provisional Patent Application No. 62/520,944, which was filed on Jun. 16, 2017.

STATEMENT REGARDING FEDERALLY SPONSORED RESEARCH OR DEVELOPMENT

This invention was made with U.S. Government support under Agreement Number W15QKN-16-3-0001 awarded by the Army Contracting Command-New Jersey (ACC-NJ). The Government has certain rights in the invention.

FIELD OF THE INVENTION

Embodiments of the present invention relate generally to the field of free space optical communication and, more specifically, to fibers, textiles, and garments capable of receiving optical wireless communication signals via free space optical communication.

BACKGROUND OF THE INVENTION

Conventional media for communication of data include wireless communication systems (e.g., WiFi), vacuum or fiber optic cable systems, hard-wired (cable) communication systems, and the like. The abundance of communication devices operating in and thereby saturating the radiofrequency (RF) domain demonstrates a need for new communication media. Advantageously, free space optical (FSO) communication provides a communication medium offering secure, line-of-sight (LoS), high-bandwidth data transmission to send information from one location to another using light.

More specifically, FSO communication propagates electromagnetic (EM) radiation through the air wherever light can travel, but only where light can travel. Advantageously, optical wireless communication systems operate in the visible to near infra-red (NIR) portion of the light spectrum, which offers $10^4$ times more bandwidth compared to the RF region of most wireless communication systems.

Until recently, the fusion of FSO technology with textiles, e.g., wearable garments, has been negligible. However, because the average human body provides 1.5 to 2 square meters of surface area, which is fertile space for receiving FSO signals, especially in the context of LoS communications, opportunities for such fusion exist.

SUMMARY OF THE INVENTION

Accordingly, it is desirable to provide a garment or other textile assembly capable of enabling the wearer to leverage the advantages of FSO communications, e.g., capable of detecting and transducing optical wireless communication signals ranging in wavelength from about 360 nm to about 2000 nm, while providing the advantages of conventional textiles, e.g., aesthetics, protection from the elements, and so forth.

In a first aspect, embodiments of the present invention provide a textile capable of detecting electromagnetic radiation. In some implementations, the textile includes interlaced fibers; a photodetector (e.g., a photodiode) embedded, as a result of a fiber draw process, within a particular one of the fibers; and a first electrical conductor (e.g., an elongate tungsten wire) extending within the particular fiber and along a longitudinal axis thereof. The first electrical conductor is in electrical contact with the photodetector, and the photodetector position in the particular fiber corresponds to a lowest energy configuration relative to a pattern of flow along the longitudinal axis of the particular fiber throughout the fiber draw process. In some applications, the photodetector is at least one of: adapted to detect an optical communication signal having a wavelength between 360 nanometers and 2,000 nanometers; and diamond-shaped when viewed in a direction perpendicular to the longitudinal axis of the particular fiber.

In some variations, the textile may also include one or more of a shielding surrounding at least a portion of the particular fiber and second and third electrical conductors extending within the particular fiber and along the longitudinal axis thereof. The second electrical conductor may be in electrical contact with the photodetector and the third electrical conductor may provide mechanical stability to the photodetector without being in electrical contact with the photodetector.

In a second aspect, embodiments of the present invention provide a system capable of detecting electromagnetic radiation using the textile described immediately above. In some implementations, the system includes the textile and an interconnect for removably coupling the first and second electrical conductors to an amplifier circuit. In some variations, the system may also include the amplifier circuit(s), which may be adapted to amplify an optical communication signal detected by the photodetector and to reject common-mode signals representative of electromagnetic interference.

In a third aspect, embodiments of the present invention provide a method of manufacturing a textile capable of detecting electromagnetic radiation. In some variations, the method includes the steps of positioning a photodetector (e.g., a photodiode) within a pocket of a preform material (e.g., a thermoplastic material) in a lowest energy configuration relative to a subsequent flow pattern of the preform material; positioning a first electrical conductor (e.g., an elongate tungsten wire) within a slot of the preform material; drawing a fiber by causing the preform material to flow; and interlacing the drawn fiber with an additional fiber(s) to form the textile. The drawing step embeds the photodetector within the fiber while maintaining the photodetector in the lowest energy configuration relative to the flow pattern of the preform material and causes the first electrical conductor to extend within the fiber along a longitudinal axis thereof and to make electrical contact with the photodetector. In some applications, the photodetector is at least one of: adapted to detect an optical communication signal having a wavelength between 360 nanometers and 2,000 nanometers and diamond-shaped when viewed in a direction perpendicular to the longitudinal axis of the drawn fiber.

In some applications, the method may also include at least one of the following steps: forming the pocket and the slot within the preform material prior to positioning the photodetector and the first electrical conductor within the preform material; shielding at least a portion of the fiber; positioning second and third electrical conductors within slots of the preform material; providing an interconnect for removably coupling the first and second electrical conductors to an amplifier circuit; and/or providing an amplifier circuit adapted to amplify an optical communication signal detected by the photodetector and to reject common-mode signals representative of electromagnetic interference. In some variations, the drawing step may cause the second electrical conductor to extend within the fiber along the longitudinal axis thereof and to make electrical contact with the photodetector and/or may cause the third electrical conductor to extend within the fiber along the longitudinal axis thereof and to provide mechanical stability to the photodetector without making electrical contact with the photodetector.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 8A shows an image of a drawn fiber resulting from drawing down a preform bar such as that shown in FIG. 7A in accordance with some embodiments of the present invention;

FIG. 8B shows an image of a drawn fiber resulting from drawing down a preform bar such as that shown in FIG. 7B in accordance with some embodiments of the present invention;

FIG. 9A shows a histogram of the distribution of chip rotation resulting from drawing down a preform bar such as that shown in FIG. 7A in accordance with some embodiments of the present invention;

FIG. 9B shows a histogram of the distribution of chip rotation resulting from drawing down a preform bar such as that shown in FIG. 7B in accordance with some embodiments of the present invention.

DETAILED DESCRIPTION

Figure 1:
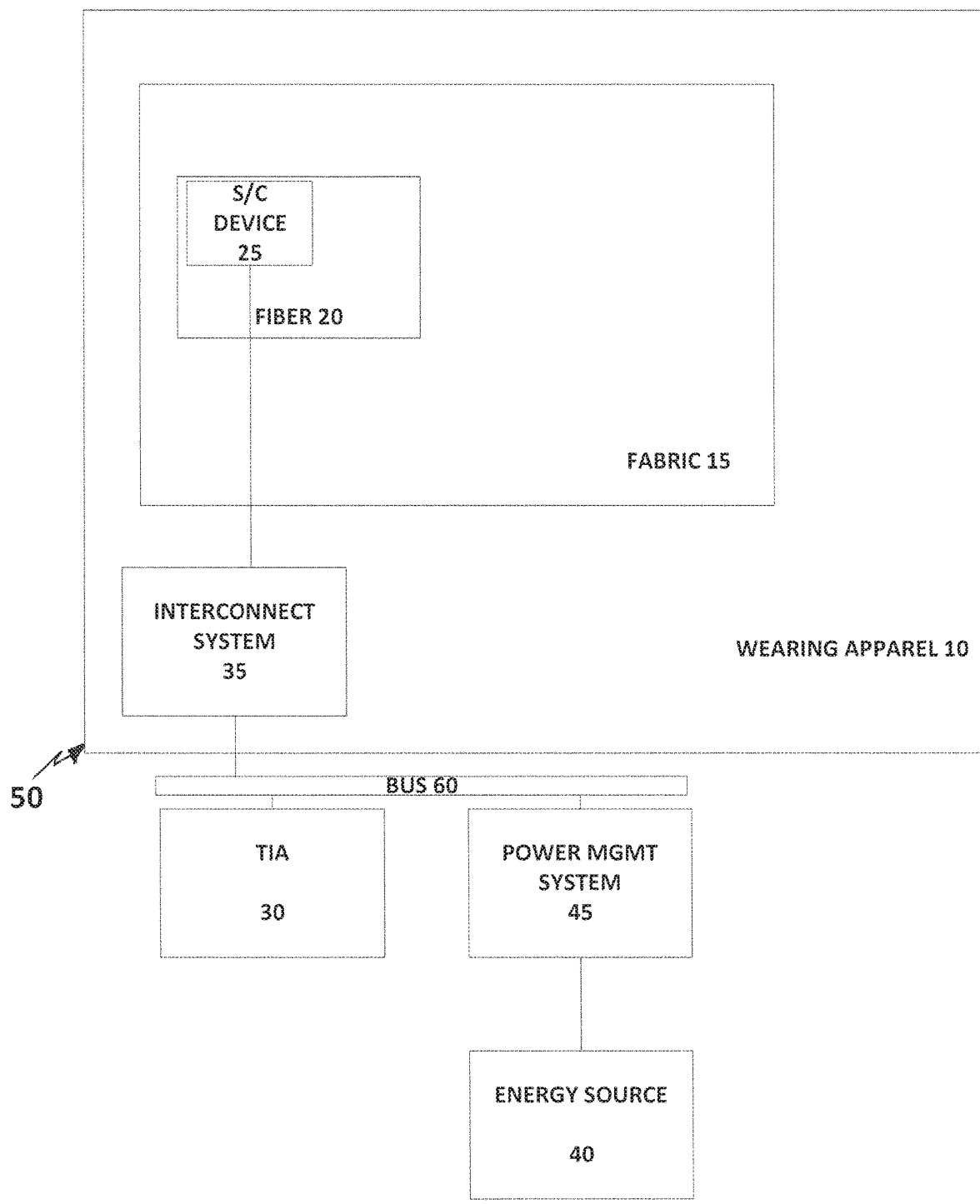
FIG. 1 shows a system capable of receiving optical wireless communication signals in accordance with some embodiments of the present invention.

Referring to FIG. 1, an illustrative embodiment of a system capable of receiving optical wireless communication signals in the visible and NIR regions of the light spectrum, for example, at wavelengths between about 360 nm and about 2000 nm, is shown. The embodied system enables the fusion and seamless integration of semiconductor technology into standard textiles, which can be used in the manufacture of wearing apparel, garments, and so forth. For example, in some embodiments, the wearing apparel 10 is made from a fabric 15 having a multiplicity of fibers 20 that have been assembled, e.g., interlaced, into a textile using conventional textile assembly methods, e.g., by weaving, by embroidery, by knitting, and the like using looms, knitting machines, and so forth. Advantageously, at least one highly functional semiconductor device, e.g., a photodiode/photodetector device 25, capable of detecting the presence of EM radiation is integrated directly into and/or embedded within one or more of the fibers 20.

Figure 2:
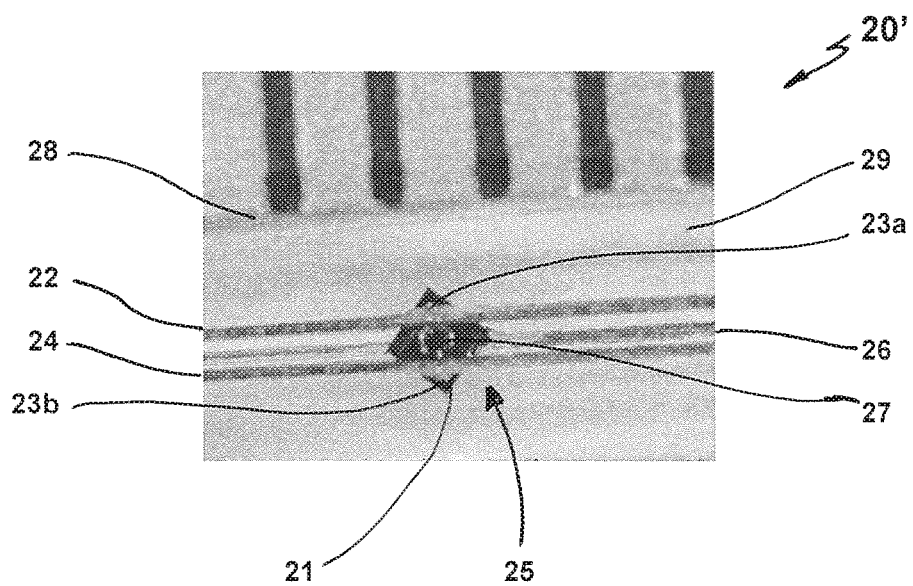
FIG. 2 is an optical micrograph of a photodiode/photodetector device embedded within a polycarbonate fiber in accordance with some embodiments of the present invention.

The system also includes an amplifier circuit or system, e.g., a small form factor, transimpedance amplifier (TIA) system 30, capable of removing electromagnetic interference (EMI) noise, especially EMI noise associated with long electrical connections within fibers, and of amplifying ultrasmall photocurrents generated by embedded photodiodes/photodetector devices 25. Integration of multiple photodiode/photodetector devices 25 within a particular fiber 20' (FIG. 2) having a cross-sectional diameter ranging between about 100 micrometers and 1000 micrometers requires the use of ultra-small chips having small light-receiving windows, apertures, or optical fibers 27 (FIG. 2). In order to convert small photocurrents that may be measured in nanoamperes into useful signals, signal amplification having large signal gains is typically required.

In some implementations, to facilitate rapid detachments of electronics, e.g., the TIA system 30, from the embedded photodiode(s)/photodetector device(s) 25 in the fibers 20, a release interconnect system 35 as part of a fiber-receiver board interconnect 50, may be provided. Advantageously, the release interconnect system 35 and fiber-receiver board interconnect 50 enable removal of the TIA system 30, an energy source 40, and any power management circuitry 45 from the wearing apparel 10 so that, for example, the wearing apparel 10 may be laundered. Removal prevents damaging any of the TIA system 30, the energy source 40, and the power management circuitry 45 while permitting normal and customary cleaning of the wearing apparel 10.

Fibers 20 assembled into a textile make up the fabric 15 of the wearing apparel 10 of the present invention. Referring to FIG. 2, one or more of the fibers integrated into the fabric 15 of the wearing apparel 10 may be a particular elongate fiber(s) 20' into which one or more semiconductor devices, e.g., photodiode(s)/photodetector device(s) 25, have been integrated and/or directly embedded. In some variations, the photodiode/photodetector device 25 may be a Gallium-Arsenide (GaAs) diode, a silicon (Si) diode, an Indium- Gallium-Arsenide (InGaAs) diode, a Mercury-Cadmium-Telleride (HgCdTe) diode, and so forth.

In one application, the fiber architecture may include a fiber matrix 29 into which a plurality of elongate wires or electrical conductors 22, 24, 26 and one or more photodiode/photodetector device(s) 25 may be integrated and/or directly embedded. The fiber matrix 29 may be manufactured from thermoplastic materials that include, for the purpose of illustration and not limitation: polycarbonate (PC), polyarylsulfones (PSU), polyetherimide (PEI), polyethylene terephthalate (PET), cyclic olefin copolymer (COC), and the like. The elongate wires 22, 24, 26 may be manufactured of tungsten, which provides excellent tensile strength and acceptable electrical conductivity. Although tungsten may not be an obvious choice for the purpose of electrical conductivity, due to the size of the fibers 20', when evaluating a tradeoff between strength and conductivity, elongate wires 22, 24, 26 made from tungsten made slicing and stripping the fibers 20' easier.

In some implementations, first 22 and second elongate wires 24 provide connections for electrical communication and electronic data communication between the photodiode/photodetector device(s) 25 and other system devices. A third elongate wire 26 may be provided to support the one or more photodiode/photodetector device(s) 25 within the fiber 20' without providing connections for electrical communication or electronic data communication. More specifically, in some variations, each photodiode/photodetector device 25 may be configured to include a planar surface 21 having a desirable geometric shape and orientation. Electrical/electronic connections or contacts 23a, 23b may be located on the planar surface 21 of a first, e.g., obverse, side of the photodiode/photodetector device 25. During manufacture via a fiber draw process, upon completion of the draw process, each of the electrical/electronic connections or contacts 23a, 23b on the obverse face of the photodiode/photodetector device 25 should be in physical contact with a respective wire of the pair of the elongate wires 22, 24 without being fixedly attached to the pair of the elongate wires 22, 24. The physical contact establishes electrical and electronic data communication between each of the one or more photodiode/photodetector device(s) 25 and, for example, the TIA system 30, the energy source 40, and/or the power management circuitry 45, e.g., via a bus 60 (FIG. 1). Advantageously, coupling the elongate wires 22, 24 with the electrical/electronic connections or contacts 23a, 23b via the fiber draw process holds the elongate wires 22, 24 in contact with the electrical/electronic connections or contacts 23a, 23b without requiring wire-bonding or other methods to fixedly attach the elongate wires 22, 24 to the electrical/electronic connections or contacts 23a, 23b.

Also, upon completion of the fiber draw process, the third elongate wire 26 is disposed against the second, e.g., reverse, side of the photodiode/photodetector device 25 to structurally support the photodiode(s)/photodetector device(s) 25 within the fiber 20'. In operation, the third elongate wire 26 located against the reverse face and the pair of the elongate wires 22, 24 located against the obverse face pinch the photodiode/photodetector device 25 between them.

To minimize rotation of the photodiode/photodetector device 25 during manufacture and to maximize the possibility of creating effective electrical contact with the photodiode/photodetector device 25, the photodiode/photodetector device 25 is oriented, at the beginning of the fiber draw process, in a lowest energy configuration relative to the pattern of flow of the fiber during the fiber draw process, which is an important factor in the manufacture of the fiber 20'. For example, square devices whose sides are initially oriented parallel (or substantially parallel) or perpendicular (or substantially perpendicular) to the longitudinal axes of the elongate wires 22, 24, 26 (and, thus, to the longitudinal axis the fiber 20') tend to rotate during manufacture, which may lead to faulty electrical connections and cause faulty electrical behavior. Square devices whose sides, in an initial orientation, are neither parallel nor perpendicular to the longitudinal axes of the elongate wires 22, 24, 26, e.g., diamond-shaped configurations when viewed in a direction perpendicular to the longitudinal axis of the fiber 20', as shown in FIG. 2, on the other hand, tend not to rotate or to rotate less during manufacture because they are already oriented in their lowest energy configuration and, thus, lead to more reliable electrical connections and produce more acceptable electrical behavior. Additional exemplary geometric shapes for the photodiode/photodetector devices 25 may include, for the purpose of illustration and not limitation, triangular, oval, circular, polygonal, and so forth.

Figure 7A:
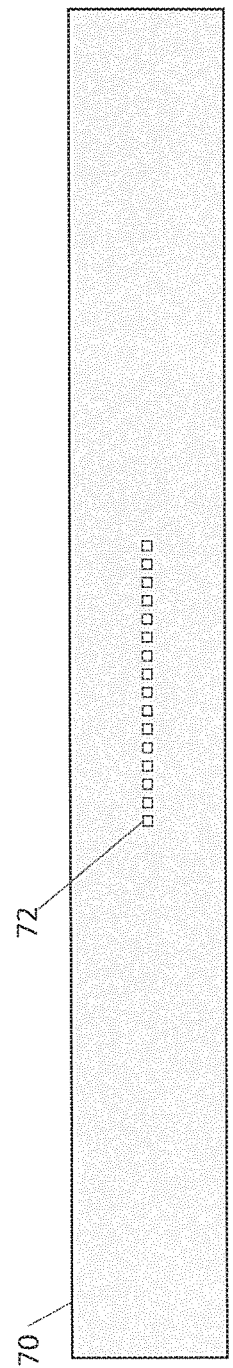
FIG. 7A shows a schematic plan view of a preform bar having plural square openings arranged in a first orientation with respect to the preform bar in accordance with some embodiments of the present invention.
Figure 7B:
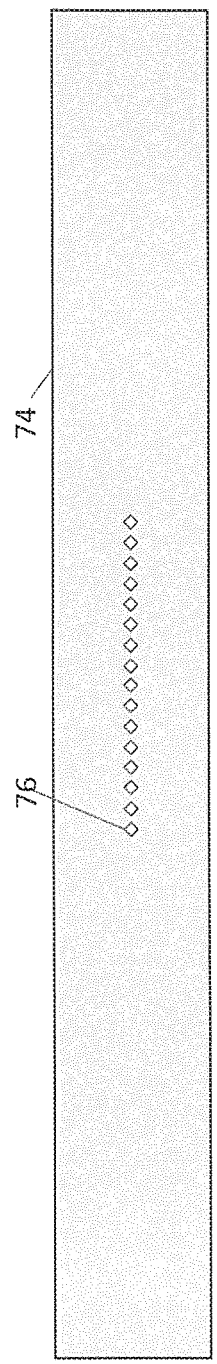
FIG. 7B shows a schematic plan view of a preform bar having plural square openings arranged in a second orientation with respect to the preform bar in accordance with some embodiments of the present invention.

The importance of photodiode/photodetector device 25 orientation in the preform bar prior to drawing the fiber (or drawing down the fiber) from a preform bar is illustrated in FIGS. 7A through 9B. FIG. 7A depicts a schematic plan view of an illustrative embodiment of a preform bar 70 having a plurality of openings or pockets 72 whose sides are initially oriented parallel (or substantially parallel) or perpendicular (or substantially perpendicular) to the longitudinal axis of the preform bar 70 and in each of which a photodiode/photodetector device 25 having the same orientation is inserted, while FIG. 7B depicts a schematic plan view of an illustrative embodiment of a preform bar 74 have a plurality of openings or pockets 76 whose sides are rotated by 45 degrees to provide a diamond-shaped configuration and in each of which a photodiode/photodetector device 25 having the same orientation is inserted. FIGS. 8A and 8B show respective images of the resulting fiber after the corresponding preform bar 70, 74 has been drawn. FIGS. 9A and 9B show respective histograms of the results of photodiode/photodetector device 25 ("chip") rotation after the fiber drawing down operation, which are summarized in Table I below.

TABLE I

Chip Rotation after Drawing Preform

| | Square (without rotation) | Square (with 45° rotation) |
|---|---|---|
| Number of Observations | 42 | 61 |
| Mean | 15.32 degrees | −2.46 degrees |
| Variance | 86.84 | 25.56 |

For square photodiode/photodetector devices 25 whose sides are initially oriented parallel (or substantially parallel) or perpendicular (or substantially perpendicular) to the longitudinal axis of the preform bar 70, the mean rotation of the photodiode/photodetector device 25 after drawing the fiber from the preform bar 70 was about 15 degrees with a variance of about 87. In contrast, when the photodiode/photodetector device 25 was first rotated by 45 degrees to provide a diamond-shaped configuration and the fiber then drawn from the preform bar 74, the mean rotation of the photodiode/photodetector device 25 after drawing the fiber was about 2 degrees with a variance of about 26, which demonstrates the value of initially orienting the photodiode/ photodetector device 25 in a lowest energy configuration relative to the pattern of flow of the fiber during the fiber draw process.

Slot distance targeting testing was also performed to estimate spatial relationships between the openings 72, 76 for photodiode/photodetector devices 25 and slots for the elongate conductive wires 22, 24 in a preform bar 70, 74 prior to draw down for a desired drawing rate (or speed) and/or draw down factor to produce a suitable fiber. In some implementations, slots may be provided in preform bars 70, 74 for receiving and retaining respective elongate conductive wires 22, 24 prior to and during draw down. Slot distance refers to the pre-draw down distance between these slots formed in the preform bars 70, 74 and, hence, the pre-draw down distance between the elongate conductive wires 22, 24.

The goal of draw down is to ensure that, after draw down, each of the elongate conductive wires 22, 24 is centered atop and/or in electrical communication with a corresponding electrical/electronic connection or contact 23a, 23b. Because the center-to-center spacing between the electrical/electronic connections or contacts 23a, 23b of the photodiode/photodetector devices 25 is, in various embodiments, fixed, manufacturers should form openings 72, 76 for the photodiode/photodetector devices 25 and slots for the elongate conductive wires 22, 24 in the preform bar 70, 74, such that, after draw down, each of the elongate conductive wires 22, 24 is centered atop and/or in electrical communication with a corresponding electrical/electronic connection or contact 23a, 23b.

Typically, the slot distance in the preform bar 70, 74 may be estimated using an empirically-determined draw down factor to scale from the known and fixed center-to-center spacing between the electrical/electronic connection or contact 23a, 23b. For example, as a starting point, if a one-inch square preform bar 70, 74 is used and a fiber having a one (1) mm dimension after draw down is desired, then the draw down factor may be 25.4, as the draw down will reduce the preform 70, 74 from dimensions of about 25.4 mm to about 1 mm. Other variables that impact the draw down factor may include, for the purpose of illustration and not limitation, the draw speed.

Figure 10:
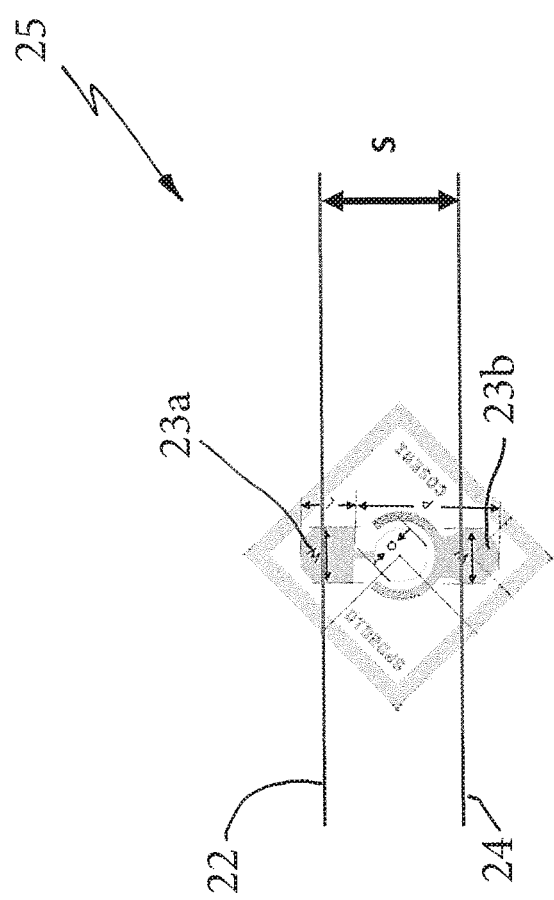
FIG. 10 shows a schematic of variables associated with slot distance targeting of a photodiode/photodetector device in accordance with some embodiments of the present invention.

Referring to FIG. 10, a photodiode/photodetector device 25 rotated by 45 degrees is shown. In some variations, the photodiode/photodetector device 25 includes a pair of rectangular electrical/electronic connections or contacts 23a, 23b, each of which has a length (L) that is measured in a direction that is perpendicular or substantially perpendicular to the fiber drawing direction and a width (W) that is measured in a direction that is parallel or substantially parallel to the fiber drawing direction. Those of ordinary skill in the art can appreciate that a pair of electrical/electronic connections or contacts 23a, 23b may, instead, be circular in shape, in which case, the width (W) and length (L) would be equal to each other and the diameter of the circular pair of electrical/electronic connection or contact 23a, 23b. The pair of electrical/electronic connections or contacts 23a, 23b also includes an edge-to-edge (or center-to-center) entitlement (P).

In some implementations, the resulting fiber after draw down may also include a pair of parallel or substantially parallel elongate conductive wires 22, 24 separated by a distance (S). Preferably and ideally, after draw down, each of the elongate conductive wires 22, 24 should be centered on a corresponding electrical/electronic connection or contact 23a, 23b, such that the distance (S) is equal to the entitlement (P), i.e., S=P. However, in practice, after draw down, as long at the distance (S) is less than the summation of the entitlement (P) and the length (L) but greater than the difference between the entitlement (P) and the length (L), i.e., P−L<S<P+L, then the resulting fiber should be suitable for use. When the distance (S) is greater than the summation of the entitlement (P) and the length (L), i.e., S>P+L, the elongate conductive wires 22, 24 will be arbitrarily located on the photodiode/photodetector device 25, such that one or both of the elongate conductive wires 22, 24 is/are not in contact with a corresponding electrical/electronic connection or contact 23a, 23b. When the distance (S) is less than the difference between the entitlement (P) and the length (L), i.e., S<P−L, the elongate conductive wires 22, 24 are likely to be in contact with one another so as to cause a short circuit.

The results of preform draw down testing for four preform targets, using a draw speed of 1600 mm/minute (mm/min.), are summarized in Table II below. Yield in the final column refers to the percentage of the photodiode/photodetector devices 25 for the respective preform that, after draw down, were suitable for use: which is to say that portions of each of the elongate conductive wires 22, 24 were in electrical communication with corresponding portions of each of the electrical/electronic connections or contacts 23a, 23b.

"Preform 11" was performed on a preform bar 70 having a photodiode/photodetector device 25 located in each of a plurality of openings 72 using empirical draw down relationships developed by others. The relationship by others includes formulae and/or recipes that assumed an empirical draw down factor (of 40) equal to the square root of the draw speed of 1600 mm/min. The openings 72 of Preform 11 included sides that were initially oriented parallel (or substantially parallel) or perpendicular (or substantially perpendicular) to the longitudinal axis of the resulting fiber. For Preform 11, whose pre-draw down distance between slot centers (or "slot space") was 5.8 mm, after draw down, at the fiber level, the average distance between the elongate conductive wires 22, 24 was 0.258, which exceeded the summation of the entitlement (P) and the length (L) and the resulting yield was zero.

"Preform 12" was performed on a preform bar 70 having a photodiode/photodetector device 25 located in each of a plurality of openings 72 after modifying the draw down relationships developed by others. The openings 72 of Preform 12 also included sides that were initially oriented parallel (or substantially parallel) or perpendicular (or substantially perpendicular) to the longitudinal axis of the resulting fiber. Preform 12 differed from Preform 11 in that the slot space at the preform level was reduced from 5.8 mm to 4.4 mm. Better results were achieved for Preform 12, for which the average distance between the elongate conductive wires 22, 24, at the fiber level after draw down, was 0.187 mm and the resulting yield was about 24%.

"Preform 24" and "Preform 31 Target" were performed on a preform bar 74 having a plurality of openings or pockets 76 whose sides were rotated by 45 degrees to provide a diamond-shaped configuration and in each of which a photodiode/photodetector device 25 having the same orientation was inserted. Using the same slot space at the preform level of 4.4 mm as that used in connection with Preform 12, the average distance between the elongate conductive wires 22, 24, at the fiber level after draw down, was 0.179 mm; however, the yield was zero. Preform 31 Target differed from Preform 24 in that the slot space at the preform level was increased from 4.4 mm to 4.76 mm. Significantly better results were achieved for Preform 31 Target, in which the average distance between the elongate conductive wires 22, 24 at the fiber level was 0.205 mm and the resulting yield was about 80%. In short, the benefits of positioning or orienting the photodiode/photodetector device 25 so as to employ a lowest energy configuration relative to a pattern of flow along the longitudinal axis of the fiber throughout the draw down process were clearly demonstrated by substantially larger yields.

TABLE II

Summary of Slot Distance Testing

| Preform Designation | Chip Orientation (in degrees) | Distance between slot centers at the preform level (mm) | Average Fiber Distance (S) between wires at the fiber level (mm) | Yield (%) |
|---|---|---|---|---|
| 11 | 0 | 5.8 | 0.258 | 0 |
| 12 | 0 | 4.4 | 0.187 | 24 |
| 24 | 45 | 4.4 | 0.179 | 0 |
| 31 Target | 45 | 4.76 | 0.205 | 80 |

Referring again to FIG. 2, a light-receiving window, aperture, or optical fiber 27 is also located on the first, e.g., obverse, side of the photodiode/photodetector device 25. The light-receiving window, aperture, or optical fiber 27 is adapted to receive light via a corresponding opening in the fiber 20'. Based on the amount of light received, electrical currents or signals are generated by the photodiode/photodetector device 25 and transmitted, e.g., via the elongate wires 22, 24, to the TIA 30. The locations of the pair of electrical/electronic connections or contacts 23a, 23b ensure that the elongate wires 22, 24 do not interfere with light entering the light-receiving window, aperture, or optical fiber 27.

Figures 3A, 3B:
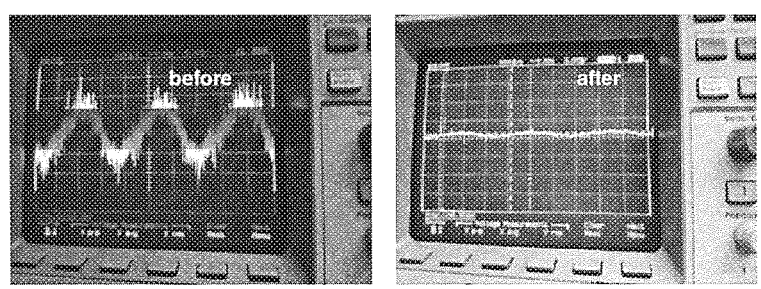
FIG. 3A shows oscilloscope traces of unshielded fibers in accordance with some embodiments of the present invention.
FIG. 3B shows oscilloscope traces of shielded fibers amplified by a non-common mode rejection circuit in accordance with some embodiments of the present invention.

The relatively long lengths of the elongate conductive wires 22, 24, 26 often cause them to act as antennae, picking up RF and EMI noise. As shown in FIG. 2, to aid in RF and EMI noise rejection, fiber-level shielding 28 may be incorporated into each fiber 20'. In some implementations, a conductive material(s), e.g., copper, gold, and the like, may be deposited, e.g., via vapor deposition, sputtering, and the like, on the peripheral surface of the fiber 20', along and about the longitudinal axis, after the fiber draw process. Special care during deposition is required to ensure that the deposited material does not cover the light-receiving window, aperture, or optical fiber 27 of any photodiode(s)/photodetector device(s) 25 embedded within the fiber 20'. Although fiber-level shielding may also be conducted during and as part of the fiber draw process, it is more difficult than application of a shield coating 28 after the fiber draw process. FIG. 3A shows oscilloscope traces of unshielded fibers, while FIG. 3B shows oscilloscope traces of shielded fibers amplified by a non-common mode rejection circuit.

Figure 4:
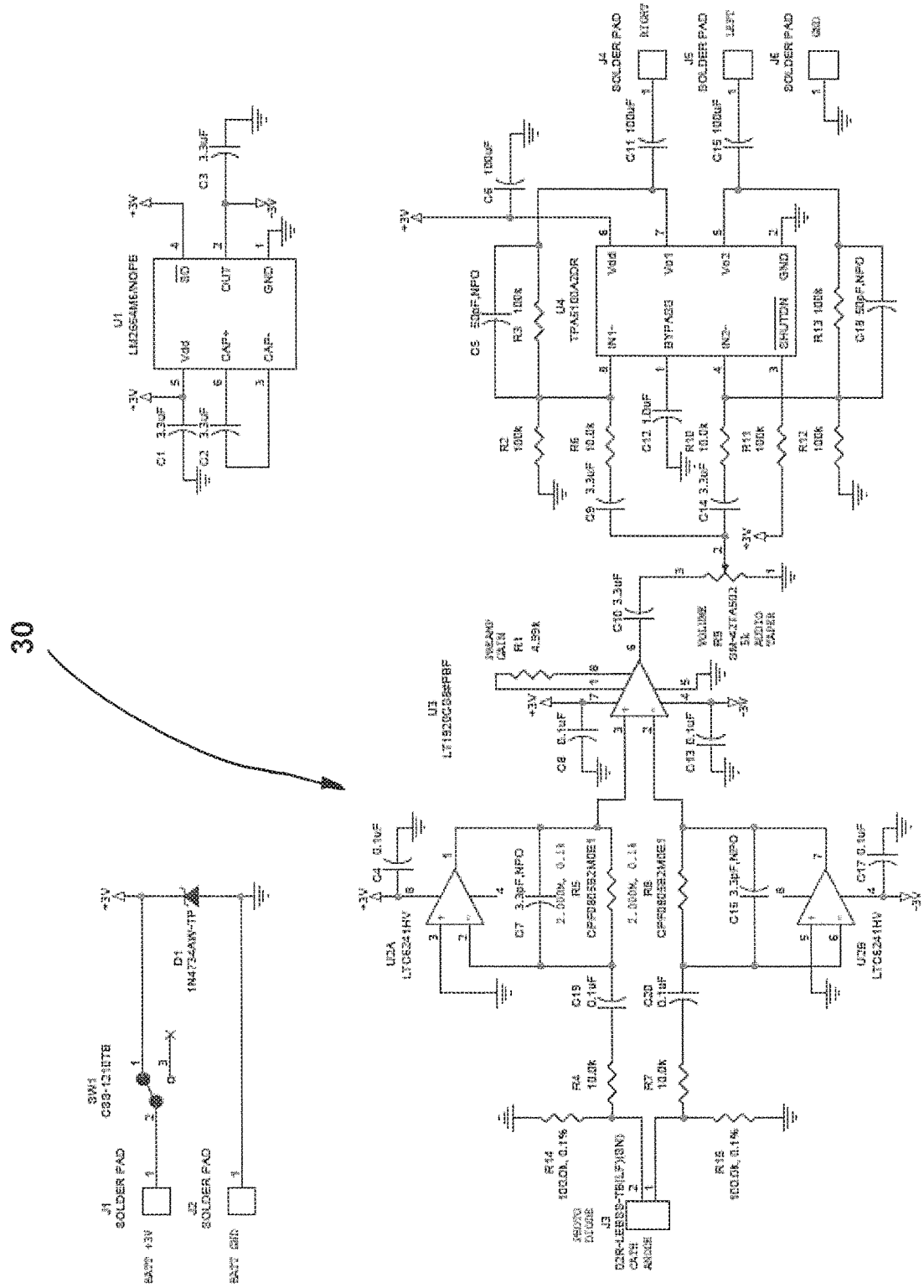
FIG. 4 shows common-mode rejection circuitry in accordance with some embodiments of the present invention.

Common-mode rejection using common-mode rejection circuitry may also be employed and serves two purposes: it supplements fiber-level shielding to reduce RF and EMI noise while also amplifying small photocurrents from the light-receiving window, aperture, or optical fiber 27 in the ultra-small photodiode/photodetector device 25 to provide a large signal gain. Referring to FIG. 4, an illustrative TIA circuit 30 for common-mode rejection to eliminate signals common to both elongate wires 22, 24 while allowing amplification of signals unique to one of the wires is shown. The exemplary TIA circuit 30 includes a first stage of differential-gain amplification and a second stage of unity-gain amplification to increase power. Common-mode rejection circuitry, including configurations other than that depicted in FIG. 4, is well known to those of ordinary skill in the art and, thus, will not be described in greater detail here. Advantageously, well-designed common-mode rejection circuitry enables amplification of currents initially measured in nanoamperes.

Figure 5:
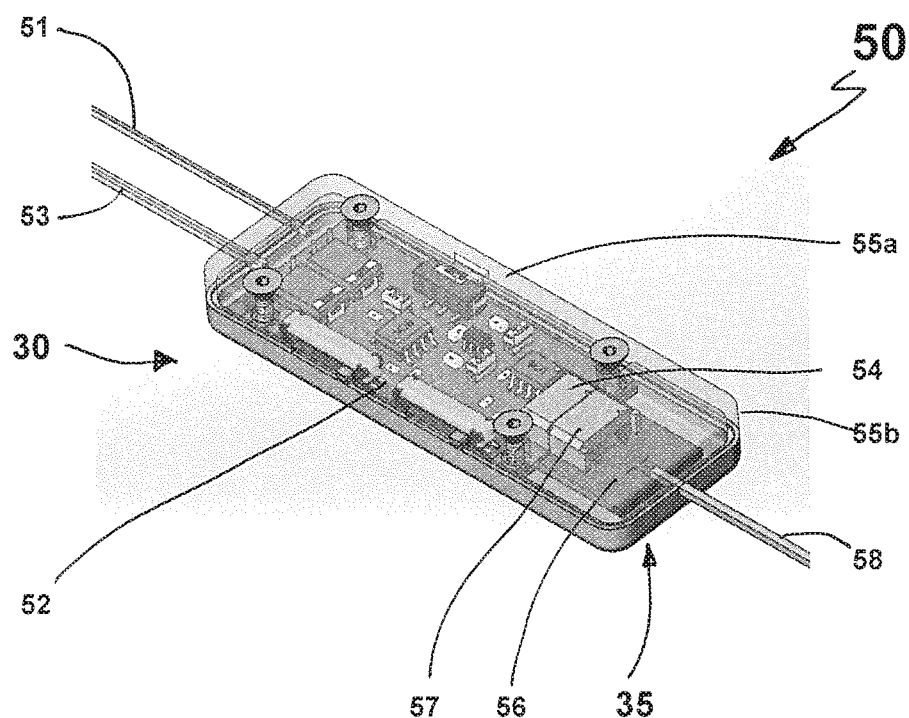
FIG. 5 shows a fiber-receiver board interconnect in accordance with some embodiments of the present invention.

Referring to FIG. 5, an embodiment of a fiber-receiver board interconnect 50 is shown. In some embodiments, the fiber-receiver board interconnect 50 includes a TIA 30 operatively coupled to a release interconnect system 35. Advantageously, the fiber-receiver board interconnect 50 allows for facile connection/disconnection of the TIA 30 (which increases the amplitude of received signals for conversion into audio and/or data signals) to/from one or more photodiodes/photodetector devices 25 embedded in one or more fibers 20'. In some implementations, the TIA 30 comprises a mother printed circuit board (PCB) 52 on which various amplification circuitry and other circuitry are laid out and operatively coupled. A first connecting port 54 is provided for mechanically connecting the TIA 30 to the release interconnect system 35. An enclosure or housing 55a protects the PCB 52 and first connecting port 54 from moisture, mechanical shock, environmental elements, and the like.

In some implementations, the release interconnect system 35 of the fiber-receiver board interconnect 50 comprises a daughter printed circuit board (PCB) 56. A second connecting port 57 is provided for mechanically connecting the release interconnect system 35 to the TIA 30 via the first connecting port 54. An enclosure or housing 55b protects the PCB 56, as well as the second connecting port 57, from moisture, mechanical shock, environmental elements, and the like.

Power, e.g., from the energy source 40, may be provided to the TIA 30 via a first multiple-conductor wire 51. Power may also be provided to the release interconnect system 35 and the photodiodes/photodetector devices 25, successively, via the first 54 and second connecting ports 57. Electronic data may be provided to/from the TIA 30 via a second multiple-conductor wire 53. Electronic data may also be provided to the release interconnect system 35 and the photodiodes/photodetector devices 25, successively, via the first 54 and second connecting ports 57. Signals from the photodiodes/photodetector devices 25 may be provided to the release interconnect system 35 via a cable 58 (e.g., using tungsten wires 22, 24) and then to the TIA 30 via the second 57 and first connecting ports 54.

Having described a textile and a system for detecting electromagnetic radiation, a method of manufacturing a textile capable of detecting electromagnetic radiation will now be described. In some embodiments, the method of manufacture involves a fiber draw process that includes drawing thermoplastic fibers containing one or more photodiodes/photodetector device(s) and one or more elongate wires (e.g., electrical conductors) embedded inside the fiber, so that electrical contact is established between each photodiode/photodetector device and one or more, e.g., two, of the elongate wires during the draw process. As previously mentioned, the fiber architecture consists of plural, e.g., three elongate wires running along the longitudinal axis of a particular fiber, as well as one or more photodiodes/photodetector devices located at discrete elevations within the fiber. During and as a result of the draw process, two of the three wires establish electrical communication with electrical contact points located on the obverse face of the photodiode/photodetector device, while the third wire provides mechanical stability to the reverse face of the photodiode/photodetector device, without establishing electrical communication with an electrical contact point on the photodiode/photodetector device.

Fibers may be drawn using standard thermoplastic draw techniques, such that a plurality of photodiodes/photodetector devices can be drawn and embedded in a single fiber. In some embodiments, the steps involved in the draw process include preparing a preform then drawing the fiber. For example, in some applications, to prepare the preform, a rectangular or square preform may be assembled using sheets and bars of a thermoplastic material that, preferably, satisfies optical and mechanical specifications of the end application. Exemplary thermoplastic materials include, for the purpose of illustration and not limitation: polycarbonate (PC), polyarylsulfones (PSU), polyetherimide (PEI), polyethylene terephthalate (PET), cyclic olefin copolymer (COC), and the like.

Prior to or while a preform is being assembled, the components of the preform may be cleaned and moisture removed. Moisture may be removed from the preform components in advance of preform assembly by drying in a vacuum oven at elevated temperature for 1-2 weeks.

In a process known as consolidation, the component pieces of the preform may be stacked together and heated (e.g., to the glass transition temperature) using a hot press or similar device in order to fuse, by heat and pressure, the various layers together. Slots for the elongate wires may be slot-milled through the longitudinal length of the preform. In some variations, to prevent a slot(s) from collapsing during subsequent consolidation steps, a (e.g., PTFE) tube may be inserted into the slot(s). Pockets for the photodiode/photodetector devices may be end-milled in the upper face of the preform at discrete locations.

Once the slots have been prepared, any inserted tube(s) may be removed and an elongate wire installed in or passed through each slot. Photodiode/photodetector devices also may be installed in each pocket. Advantageously, the most effective orientation of the photodiode/photodetector device when installed within the pocket is that which provides a lowest energy configuration relative to the pattern of flow of the fiber during the fiber draw process. Consequently, when viewed in a direction perpendicular to the longitudinal axis of the fiber, the lowest energy configuration for rectangular (e.g., square) photodiode/photodetector devices corresponds to a diamond-shaped orientation in which the sides of the rectangular photodiode/photodetector device are neither substantially parallel nor substantially perpendicular to the longitudinal axis of the preform. This geometric configuration of the photodiode/photodetector device within the preform minimizes rotation of the photodiode/photodetector device during drawing and maximizes the possibility of creating electrical contact between the elongate wires and the photodiode/photodetector device. In contrast, devices oriented in a square fashion, in which the sides of the square are parallel or perpendicular or substantially parallel and substantially perpendicular to the longitudinal axis of the preform, tend to rotate during the draw process, which may lead to faulty electrical connections and cause faulty behavior within the resulting fibers.

The shape of current commercially-available photodetector devices is rectangular or square, for which a photodiode/photodetector device having a diamond-shaped orientation provides a lowest energy configuration relative to a pattern of flow along the longitudinal axis of the particular fiber throughout the fiber draw process. Those of ordinary skill in the art can appreciate that photodiode/photodetector device manufacturers may, in the future, manufacture such devices in triangular, polygonal, circular, oval, and other shapes.

To protect the photodiode/photodetector device during the draw process, a (e.g., PC) sheet may be placed over the photodiode/photodetector device and the exposed pocket opening on the upper face of the preform. Small holes may be installed (e.g., drilled) into one end of the preform and a weight or body of mass suspended from or mounted to the preform.

In a next step, the preform may then be mounted to a draw tower within, for example, a three-zone furnace. The thermoplastic material of the preform is heated until it begins to flow under the force of the weight or mass body attached to the bottom of the preform. As the fiber is drawn from the preform, each of the elongate wires align with the photodiode/photodetector devices, such that, in some applications, two of the elongate wires physically contact an obverse face of the photodiode/photodetector device, and, more specifically, advantageously create an electrical communication with the photodiode/photodetector device, while the third wire physically contacts the reverse face of the photodiode/photodetector device, however without establishing any electrical contact. Contact between the two elongate wires against its obverse face and the one elongate wire against its reverse face captures the photodiode/photodetector device between the three elongate wires, supporting the photodiode/photodetector device within the fiber.

Once a fiber emerges from the furnace it is attached to a capstan/winder system, which winds the fiber at a controlled rate. The temperature of the furnace coupled with the winding rate and the rate at which the preform is lowered into the furnace controls the overall diameter of the fiber.

Figures 6A, 6B, 6C:
FIGS. 6A through 6C show various garments and pieces of apparel into which fibers in accordance with some embodiments of the present invention have been integrated.

FIGS. 6A-6C show representative uses of the particular fibers incorporated into wearable apparel (e.g., a vest (FIG. 6A) and a hat (FIGS. 6B and 6C). In an illustrative example of free space optical communication, information, e.g., music, may be transmitted (e.g., as a modulated visible light signal) via a light emitting diode (LED) device located, for example, in a ceiling tile. Responding to the modulated visible light signal, photodiodes/photodetector devices, embedded in one or more fibers integrated into the fabric of a vest or a hat, and with a line-of-sight to the transmitting LED, detect the signal and generate a time-varying current, which is on the order of a few nanoamperes. The TIA circuit, which may be embedded, e.g., in the sweatband of the hat or within the collar of the vest, amplifies the signal. The amplified photocurrent may then be used to drive any device capable of transducing electrical signals (e.g., a portable speaker, a set of headphones, and the like) that is in electronic data communication with the TIA circuit, thereby delivering the music to the wearer of the vest or hat.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A textile capable of detecting electromagnetic radiation, the textile comprising:
  a plurality of interlaced fibers;
  a photodetector embedded, as a result of a fiber draw process, within a particular one of the plurality of fibers; and a first electrical conductor extending within the particular fiber and along a longitudinal axis thereof, the first electrical conductor in electrical contact with the photodetector, wherein the photodetector position in the particular fiber comprises a lowest energy configuration relative to a pattern of flow along the longitudinal axis of the particular fiber throughout the fiber draw process.

2. The textile of claim 1, wherein the photodetector comprises a photodiode.

3. The textile of claim 1, wherein the photodetector is adapted to detect an optical communication signal having a wavelength between 360 nanometers and 2,000 nanometers.

4. The textile of claim 1, wherein the photodetector is diamond-shaped when viewed in a direction perpendicular to the longitudinal axis of the particular fiber.

5. The textile of claim 1, wherein the first electrical conductor comprises tungsten.

6. The textile of claim 1 further comprising shielding surrounding at least a portion of the particular fiber.

7. The textile of claim 1 further comprising second and third electrical conductors extending within the particular fiber and along the longitudinal axis thereof, the second electrical conductor in electrical contact with the photodetector and the third electrical conductor providing mechanical stability to the photodetector without being in electrical contact with the photodetector.

8. A system capable of detecting electromagnetic radiation, comprising:

the textile of claim 7; and an interconnect for removably coupling the first and second electrical conductors to an amplifier circuit.

9. The system of claim 8 further comprising the amplifier circuit, wherein the amplifier circuit is adapted to amplify an optical communication signal detected by the photodetector and to reject common-mode signals representative of electromagnetic interference.

10. A method of manufacturing a textile capable of detecting electromagnetic radiation, the method comprising the steps of:

positioning a photodetector within a pocket of a preform material in a lowest energy configuration relative to a subsequent flow pattern of the preform material;

positioning a first electrical conductor within a slot of the preform material;

drawing a fiber by causing the preform material to flow, wherein the drawing step i) embeds the photodetector within the fiber while maintaining the photodetector in the lowest energy configuration relative to the flow pattern of the preform material, and ii) causes the first electrical conductor to extend within the fiber along a longitudinal axis thereof and to make electrical contact with the photodetector; and interlacing the drawn fiber with at least one additional fiber to form the textile.

11. The method of claim 10, wherein the photodetector comprises a photodiode.

12. The method of claim 10, wherein the photodetector is adapted to detect an optical communication signal having a wavelength between 360 nanometers and 2,000 nanometers.

13. The method of claim 10, wherein the photodetector is diamond-shaped when viewed in a direction perpendicular to the longitudinal axis of the drawn fiber.

14. The method of claim 10, wherein the preform material comprises a thermoplastic material.

15. The method of claim 10, wherein the first electrical conductor comprises tungsten.

16. The method of claim 10 further comprising forming the pocket and the slot within the preform material prior to positioning the photodetector and the first electrical conductor within the preform material.

17. The method of claim 10 further comprising the step of shielding at least a portion of the fiber.

18. The method of claim 10 further comprising positioning second and third electrical conductors within slots of the preform material.

19. The method of claim 18, wherein the drawing step further causes a) the second electrical conductor to extend within the fiber along the longitudinal axis thereof and to make electrical contact with the photodetector, and b) the third electrical conductor to extend within the fiber along the longitudinal axis thereof and to provide mechanical stability to the photodetector without making electrical contact with the photodetector.

20. The method of claim 19 further comprising providing an interconnect for removably coupling the first and second electrical conductors to an amplifier circuit.

21. The method of claim 20, further comprising providing the amplifier circuit, wherein the amplifier circuit is adapted to amplify an optical communication signal detected by the photodetector and to reject common-mode signals representative of electromagnetic interference.

* * * * *